Figure 1:
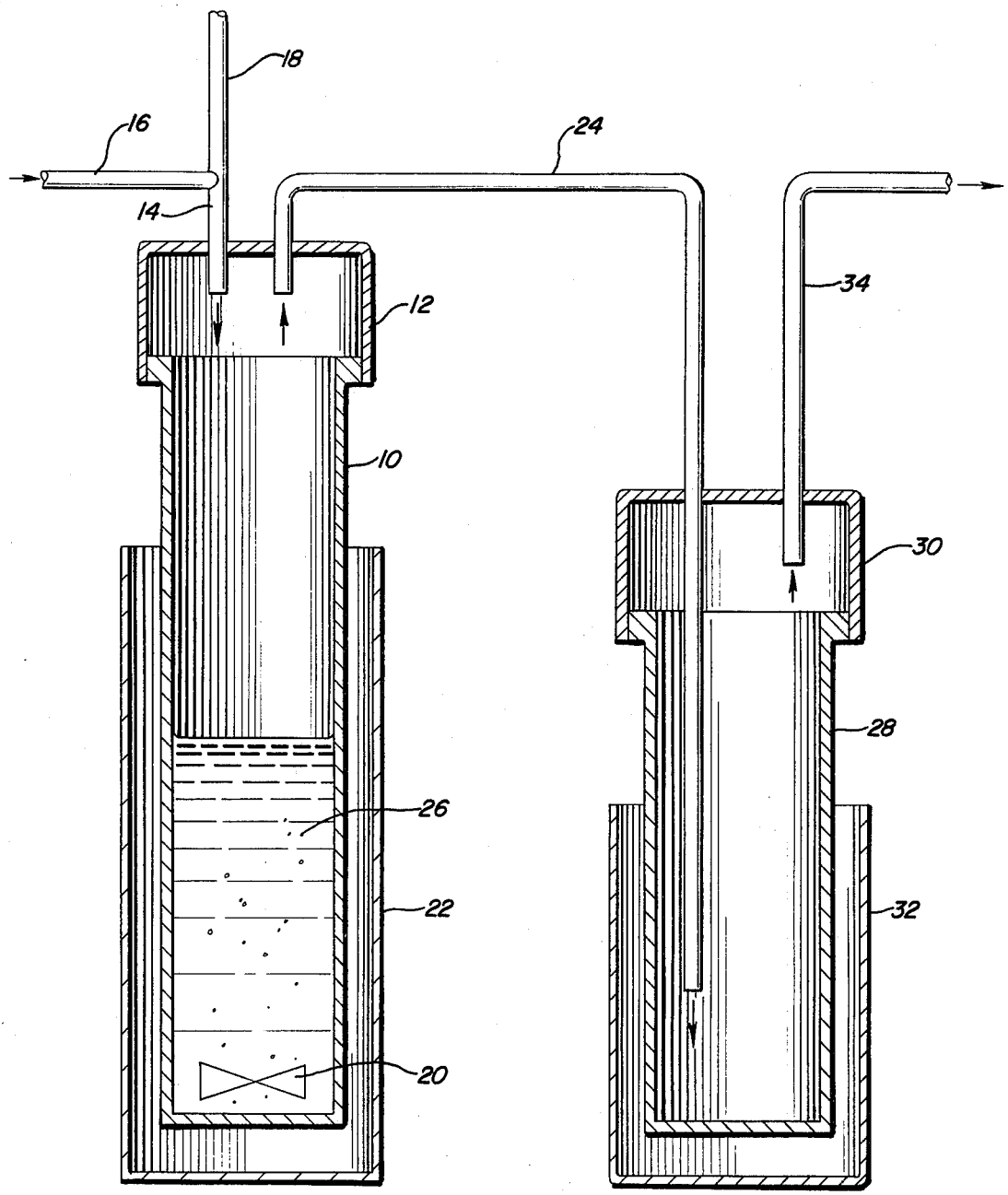

United States Patent [19]

Coon et al.

[11] 4,250,334

[45] Feb. 10, 1981

[54] METHOD OF SYNTHESIZING FLUOROMETHYLHEXAFLUOROISOPROPYL ETHER

[75] Inventors: Clifford L. Coon, Fremont; Robert L. Simon, San Carlos, both of Calif.

[73] Assignee: Baxter Travenol Laboratories, Inc., Deerfield, Ill.

[21] Appl. No.: 107,117

[22] Filed: Dec. 26, 1979

[51] Int. Cl.$^3$ .................... C07C 41/01; C07C 41/42
[52] U.S. Cl. .................................. 568/683; 568/682
[58] Field of Search ........................................ 568/683

[56] References Cited

U.S. PATENT DOCUMENTS

| | | | |
|---|---|---|---|
| 2,992,276 | 7/1961 | Weynmayr | 568/842 X |
| 3,683,092 | 8/1972 | Regan et al. | 568/683 UX |
| 3,689,571 | 9/1972 | Regan et al. | 568/683 |

*Primary Examiner*—Howard T. Mars
*Attorney, Agent, or Firm*—Paul C. Flattery; Lawrence W. Flynn; Max D. Hensley

[57] ABSTRACT

A method of synthesizing fluoromethylhexafluoroisopropyl ether comprises adding hexafluoroisopropyl alcohol to a mixture comprising a stoichiometric excess of paraformaldehyde and hydrogen fluoride, plus sufficient sulfuric acid to sequester most of the water produced by the reaction. The mixture is maintained at a temperature of at least 57° C., to cause vapor formation by boiling of the fluoromethylhexafluoroisopropyl ether formed. The vapor is then collected and condensed, and may be purified by distillation.

16 Claims, 1 Drawing Figure

METHOD OF SYNTHESIZING FLUOROMETHYLHEXAFLUOROISOPROPYL ETHER

BACKGROUND OF THE INVENTION

Fluoromethyl-1,1,1,3,3,3-hexafluoroisopropyl ether, as described in U.S. Pat. Nos. 3,683,092 and 3,689,571, is a promising new anesthetic for human use which is essentially non-inflammable, and appears to have few or no undesirable side effects when administered to humans.

In the abandoned U.S. patent application Ser. No. 771,365, filed Oct. 28, 1968, from which the above two patents claim priority, several techniques are suggested which may be used for making ethers having halogen groups in both of the organic ether substituents, including fluoromethylhexafluoroisopropyl ether. It is suggested there that the corresponding alcohol may be reacted with formaldehyde and hydrogen fluoride to form the fluoromethyl ether. However, yields of this reaction generally described in the abandoned patent application cited above, are not of a desired commercial scale, so other, more cumbersome, multiple step synthesis routes were initially preferred. Weynmayr U.S. Pat. No. 2,992,276 also teaches the use of paraformaldehye and hydrogen fluoride as a reagent for synthesizing a fluoromethylether and an alcohol from tetrafluoroethylene.

In accordance with this invention, a simplified, high yield synthesis technique for fluoromethylhexafluoroisopropyl ether is disclosed, capable of producing yields of the desired ether product of the order of 90 percent, with recycling of unused reactants through the reaction mixture for optimization of synthesis. Particularly, fluoromethyl-1,1,1,3,3,3-hexafluoroisopropyl ether may be made this way as a clinical anesthetic on a large scale basis.

DESCRIPTION OF THE INVENTION

In accordance with this invention, fluoromethylhexafluoroisopropyl ether may be synthesized by adding 1,1,1,3,3,3-hexafluoroisopropyl alcohol to a mixture containing a stoichiometric excess of formaldehyde (preferably paraformaldehyde) and hydrogen fluoride, plus sufficient sulfuric acid to sequester most of the water produced by the reaction. The reaction mixture is maintained at a temperature of at least 57° C. (which is the boiling point of fluoromethyl-1,1,1,3,3,3- hexafluoroisopropyl ether) to cause vapor formation by boiling of the ether product formed. Accordingly, the ether product which is formed is quickly removed from the reaction mixture by boiling, which greatly reduces degradation of the ether product by the strongly acidic reaction mixture.

The vapors of the ether product are then collected and condensed, for example with conventional distillation equipment, to collect the impure fluoromethylhexafluoroisopropyl ether product. Thereafter, the ether product may be purified, preferably by a conventional distillation technique, with the hexafluoroisopropyl alcohol wich is co-distilled with the ether product being returned, if desired, to the reaction mixture. The deuterium-containing analog of the above alcohol may be used if desired, or deuterated formaldehyde, to form a deuterated ether product.

Byproducts of the reaction may also be removed by conventional distillation, or other known purification techniques.

The term "formaldehyde" as used herein is intended to include polymers thereof as well as the monomer, such as trioxane or the preferred paraformaldehyde.

Preferably, the temperature of the reaction mixture is maintained at 60 to 70 degrees, with the hexafluoroisopropyl alcohol being added on a continuous, gradual basis. This permits the rapid distillation of the ether product, which is rapidly distilled out of the reaction mixture, and the codistilled alcohol reactant being returned to the mixture after separation from the ether product, until the formaldehyde and hydrogen fluoride reactants become reduced to a concentration insufficient to provide the desired high yields of ether product.

Preferably, at least a 10 to 100 percent molar excess of formaldehyde is present in the reaction mixture, based on the total amount of the hexafluoroisopropyl alcohol added.

Also, at least a 400 to 1000 percent molar excess of hydrogen fluoride is preferably present, based upon the total amount of hexafluoroisopropyl alcohol added.

It is also preferable for a greater weight of generally anhydrous (preferably at least 95 percent) sulfuric acid to be present, when compared with the total weight of the formaldehyde present. Preferably, from 50 to 200 percent greater weight of the generally anhydrous sulfuric acid is present.

It is also contemplated that other ingredients such as solvents, catalysts, diluents, and other materials may also be present in the reaction mixture if desired, as long as the added extraneous materials do not materially change the nature of the reaction described above, but are added to promote the reaction, suppress side reactions, improve the purification step of the synthesis, etc.

The example described below is presented for illustrative purposes only, and is not intended to limit the scope of the invention of this application, which is as defined in the claims below.

EXAMPLE

To 3.0 grams by weight (0.1 mol) of paraformaldehyde there was added 5 ml. of 96 percent sulfuric acid and 10 grams (0.5 mol) of hydrogen fluoride. This reaction mixture was heated to 65° C. Thereafter, there was added on a dropwise basis, over one hour, 13.4 grams (0.08 mol) of 1,1,1,3,3,3-hexafluoroisopropyl alcohol.

During this period, vapors were generated on the dropwise addition of the alcohol reactant, which vapors were collected in a cooled collector of a distillation set over a period of two hours, using the nitrogen sweep technique and apparatus shown in FIG. 1 and described below.

Thereafter, the material obtained in the cooled collector at the end of the two hours was quenched on ice, neutralized with ammonia, and distilled.

The material from the cooled collector gave two fractions on distillation. Fraction (1) distilled between 25° and 58° C., to provide a yield of 6.7 grams of material. Fraction (1) was found upon analysis to yield 90 percent by weight fluoromethyl-1,1,1,3,3,3-hexafluoroisopropyl ether, 3 percent by weight of the initial alcohol reaction material, and 7 percent of a formal byproduct, the analysis being by Gas Chromatographic Analysis.

Fraction (2) from the cooled collector distilled between 58° and 95° C. to yield 5.5 grams of material. This fraction contained 11 percent by weight of fluoromethyl-1,1,1,3,3,3-hexafluoroisopropyl ether, 42 percent of the alcohol starting material, 33 percent of a formal byproduct, and 13 percent of an acetal byproduct, the analysis being again by Gas Chromatographic Analysis.

It appears that the fluoromethyl-1,1,1,3,3,3-hexafluoroisopropyl ether can be obtained in greater than a 90 percent yield, at between 33 and 38 percent conversion, based upon the recovered alcohol reactant from fraction (1). It is, however, also possible that some water may azeotrope during the distillation process, which may tend to suppress the yields. This can be controlled to a significant extent by the concentration of sulfuric acid present, which can sequester water that is formed in the reaction.

The recovered alcohol reactant and byproducts are readily separable from the ether product, and then may be recycled back to the reaction mixture for the production of more ether product.

In the drawing, FIG. 1 is a schematic view of the reaction apparatus used for performing the reaction described above, with further details of the reaction technique added.

Referring to FIG. 1, reaction vessel 10, made of Kel-F fluorinated plastic and sealed with closure 12, defines an inlet line 14 which has a branch connection. One of the connections 16 is connected to a source of pressurized nitrogen gas, and the other connection 18 is connected to a source of hexafluoroisopropyl alcohol. The reaction vessel 10 is equipped with a magnetic stirring bar 20, and positioned within an oil bath 22 for control of the temperature of the reaction mixture at, preferably, about 65° C.

Tubular outlet line 24 communicates with container 10 and carries vapors generated by the reaction mixture 26, which contains the paraformaldehyde, hydrogen fluoride, and sulfuric acid reactants, to a collector container 28 made of Kel-F fluorinated plastic. Container 28 also defines closure 30 with line 34 sealingly passing through it. Container 28 is also placed in a cooling bath 32 to assist in condensation of the vapors in container 32.

Vent line 34 communicates with the exterior. Accordingly, nitrogen gas may be constantly used to provide a low velocity gas sweep through the reaction system, while the alcohol reactant is added dropwise through inlet line 18. The vapors which are generated leave reaction chamber 10 through line 24, and are condensed in container 28. The sweeping nitrogen gas then continues to pass outwardly through vent 34, while the products and byproducts of the reaction are collected in the collector container 28.

Periodically, the collector container 28 may be empties of its contents, with the ether product being purified and separated from the alcohol reactant and its byproducts. The reactant and byproducts may be returned to the reaction mixture for further production of the ether product. The byproducts, in turn, tend to suppress the creation of more byproducts in the reaction mixture by the principles of chemical equilibrium. Alternatively, they may be separated for use or further processing.

That which is claimed is:

1. The method of synthesizing fluoromethyl-1,1,1,3,3,3-hexafluoroisopropyl ether which comprises adding hexafluoroisopropyl alcohol to a mixture comprising a stoichiometric excess of formaldehyde and hydrogen fluoride, plus sufficient sulfuric acid to sequester most of the water produced by the reaction, said mixture being maintained at a temperature of at least 57° C. to cause vapor formation by boiling of the fluoromethylhexafluoroisopropyl ether formed; and collecting and condensing said vapor.

2. The method of claim 1 including the step of thereafter purifying fluoromethylhexafluoroisopropyl ether from said condensed vapor.

3. The method of claim 1 in which said formaldehyde is paraformaldehyde.

4. The method of claim 1 in which said mixture is maintained at a temperature of 60° to 70° C.

5. The method of claim 1 in which said hexafluoroisopropyl alcohol is added on a continuous, gradual basis.

6. The method of claim 1 in which at least a 10 percent molar excess of paraformaldehyde is present, based on the hexafluoroisopropyl alcohol added.

7. The method of claim 6 in which at least a 400 percent molar excess of hydrogen fluoride is present, based on the hexafluoroisopropyl alcohol added.

8. The method of claim 7 in which a greater weight of generally anhydrous (at least 95 percent) sulfuric acid is present when compared with the weight of the paraformaldehyde present.

9. The method of claim 1 in which from 10 to 100 molar percent excess of paraformaldehyde and 400 to 1000 molar percent excess of hydrogen fluoride is present.

10. The method of claim 9 in which a 50 to 200 percent greater weight of generally anhydrous (at least 95 percent) sulfuric acid is present, compared with the weight of the paraformaldehyde present.

11. The method of synthesizing fluoromethyl-1,1,1,3,3,3-hexafluoroisopropyl ether which comprises adding 1,1,1,3,3,3-hexafluoroisopropyl alcohol to a mixture comprising a stoichiometric excess of paraformaldehyde and hydrogen fluoride, plus sufficient sulfuric acid to sequester most of the water produced by the reaction, said mixture being maintained at a temperature of 60 to 70 degrees to cause vapor formation by boiling of the fluoromethyl-1,1,1,3,3,3-hexafluoroisopropyl ether formed; collecting and condensing said vapor; and thereafter purifying by distillation said fluoromethyl-1,1,1,3,3,3-hexafluoroisopropyl ether from said condensed vapor, said hexafluoroisopropyl alcohol being added to the mixture on a continuous, gradual basis.

12. The method of claim 11 in which at least a 10 percent molar excess of paraformaldehyde is present, based on the hexafluoroisopropyl alcohol added.

13. The method of claim 12 in which at least a 400 percent molar excess hydrogen fluoride is present, based on the hexafluoroisopropyl alcohol added.

14. The method of claim 13 in which a greater weight of generally anhydrous (at least 95%) sulfuric acid is present, compared with the weight of the paraformaldehyde present.

15. The method of claim 11 in which a 10 to 100 mole percent excess of paraformaldehyde and a 400 to 1000 mole percent excess of hydrogen fluoride is present.

16. The method of claim 15 in which a 50 to 200 percent greater weight of generally anhydrous (at least 95 percent) sulfuric acid is present, compared with the weight of the paraformaldehyde present.

* * * * *

UNITED STATES PATENT AND TRADEMARK OFFICE

CERTIFICATE EXTENDING PATENT TERM
UNDER 35 U.S.C. § 156

PATENT NO. : 4,250,334

ISSUED : February 10, 1981

INVENTOR(S) : Clifford L. Coon, et al.

PATENT OWNER : Baxter International, Inc.

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of Five Years from the original expiration date of the patent, December 26, 1999, with all rights pertaining thereto as provided by 35 U.S.C. § 156(b).

I have caused the seal of the Patent and Trademark Office to be affixed this 6th day of January 1997.

Bruce A. Lehman
Assistant Secretary of Commerce and
  Commissioner of Patents and Trademarks